United States Patent [19]
De La Torre et al.

[11] Patent Number: 5,267,949
[45] Date of Patent: Dec. 7, 1993

[54] POSITIONING DEVICE FOR A LOWER EXTREMITY

[75] Inventors: Manuel De La Torre, 2369 W. Hardies Rd., Gibsonia, Pa. 15044; Thomas K. Donaldson, 758 S. Center St., Redlands, Calif. 92373

[73] Assignees: Manuel De La Torre, Pittsburgh, Pa.; Thomas Kent Donaldson, Redlands, Calif.

[21] Appl. No.: 856,252

[22] Filed: Mar. 25, 1992

[51] Int. Cl.$^5$ ............................................. A61F 5/00
[52] U.S. Cl. ...................... 602/24; 602/23; 128/882
[58] Field of Search ............ 128/25 R, 25 B, 845, 128/869, 878, 879, 881, 882; 602/5, 23-29; 5/648, 650, 651

[56] References Cited
U.S. PATENT DOCUMENTS

| | | | |
|---|---|---|---|
| 3,171,407 | 3/1965 | Rogers | 602/24 |
| 3,304,937 | 2/1967 | Callender, Jr. | 602/25 |
| 4,320,749 | 3/1982 | Highley | 602/27 |
| 4,323,080 | 4/1982 | Melhart | 128/882 X |
| 4,665,899 | 5/1987 | Farris et al. | 128/25 R |
| 4,669,722 | 6/1987 | Rangaswamy | 128/25 B X |
| 4,795,148 | 1/1989 | Rangaswamy | 128/25 B X |
| 4,827,496 | 5/1989 | Cheney | 5/651 X |

Primary Examiner—Richard J. Apley
Assistant Examiner—Linda C. M. Dvorak
Attorney, Agent, or Firm—Webb, Burden, Ziesenheim & Webb

[57] ABSTRACT

A positioning device for positioning the lower extremity to aid in CAT scan diagnostics is disclosed with the purpose being to lock the hip joint in degrees of external or internal rotation. The positioning device includes a base board with an upright plate rigidly attached to the board and a boot for receiving the lower extremity with locking means to lock the boot to the plate and base board at various orientations.

12 Claims, 2 Drawing Sheets

POSITIONING DEVICE FOR A LOWER EXTREMITY

BACKGROUND OF THE INVENTION

The present invention relates to a positioning device for a lower extremity to aid in CAT scan diagnostics and, more specifically, is related to positioning devices for locking the hip joint in position at specific degrees of external or internal rotation.

In the process of a CAT scan, total immobility of the specific extremity is required. Since the CAT scan is a lengthy procedure, having the patient maintain the extremity in the desired orientation has proven unsatisfactory. The patient simply cannot keep the extremity motionless in the desired orientation throughout the CAT scan procedure, thereby adversely affecting the results of the CAT scan. Furthermore, the process of taping or supporting the patient's extremity in the desired orientation on an ad hoc basis has proved to be cumbersome, time-consuming and inaccurate. The available supports which could be utilized to help maintain the patient's extremity in position are limited by the amount of space present in CAT scan machinery.

SUMMARY OF THE INVENTION

It is an object of the present invention to provide a positioning device for a lower extremity to aid in CAT scan diagnostics. It is a further object to provide a positioning device to lock the hip joint in position at specific degrees of external or internal rotation. There is an additional object of the present invention to design a positioning device which would operate within the limited confines of space provided in CAT scan machinery.

The present invention is a positioning device for a lower extremity which includes a base board, a reinforcing plate which may be attached to the lower portion of the base board, and an upright plate attached at a right angle to the base board and the reinforcing plate, if present. A boot is provided for receiving the patient's lower extremity and locking means for attaching the boot to the upright plate at various orientations relative to the plate to thereby securely locate and position the patient's extremity at the desired orientation. The boot itself includes a removable, soft inner wrap and a hard outer layer. The bottom of the boot includes a shaped subsole provided with soft rubber padding.

The present invention improves over the prior art in that it provides a device that maintains a desired orientation through the lengthy process of a CAT scan and provides for quick, accurate positioning of the lower extremity and rotational orientation of the hip joint. The device of the present invention is also designed to be operable within the limited confines of space available in CAT scan machinery.

The present invention is primarily intended for use during diagnostic CAT scan procedures. However, the positioning device of the present invention may be utilized during other diagnostic procedures, rehabilitative procedures or operations where maintaining the patient's lower extremity in a specific orientation is desired.

Further objects and advantages of the present invention will become apparent through the description of the present invention in connection with the attached drawings.

DESCRIPTION OF THE PREFERRED EMBODIMENTS

Figure 1:
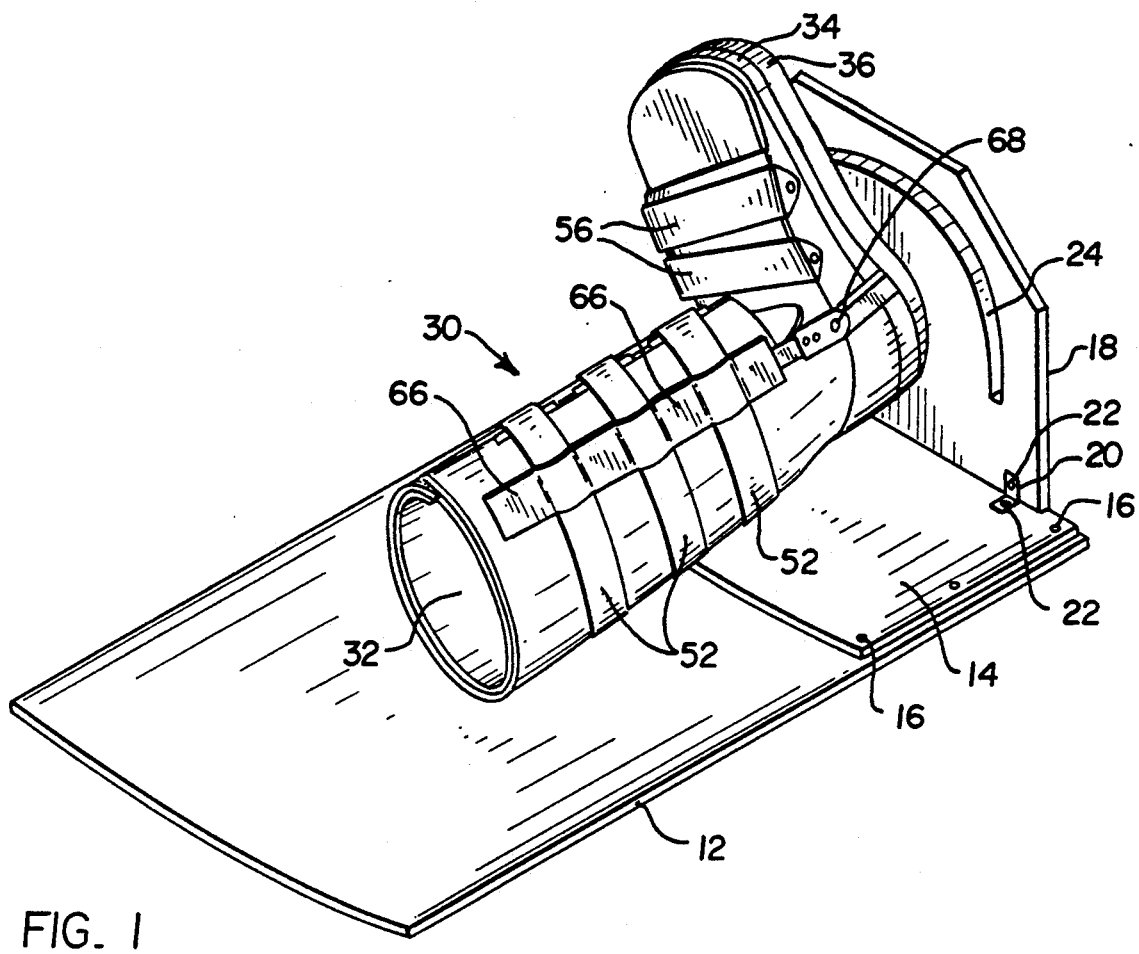
FIG. 1 is an elevational, perspective view of the positioning device of the present invention.
Figure 2:
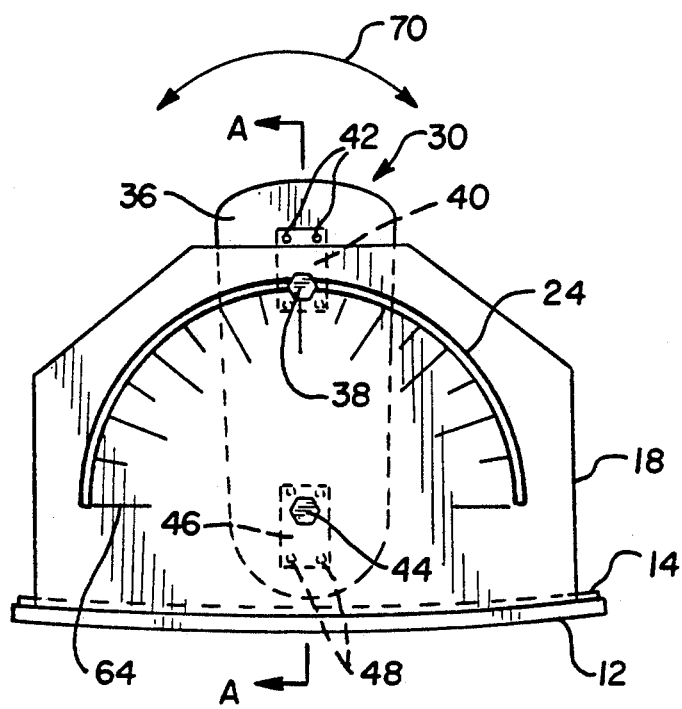
FIG. 2 is a front view of the positioning device of FIG. 1.

The positioning device 10 for a lower extremity, shown in FIGS. 1-4, was designed to aid in CAT scan diagnostics. The purpose of the positioning device 10 is to position the lower extremity in the desired orientation and to lock the hip joint in position at specific degrees of external or internal rotation. The positioning device 10, as noted above, is not limited for use in CAT scan diagnostics, but is applicable to a variety of diagnostic and rehabilitative uses and operational procedures in which the lower extremity is needed to be held in a specific rotational orientation.

The positioning device 10 includes a base board 12 which serves as a supporting base for the attached positioning boot 30. The base board 12 may be formed as a flat, rectangular plate or, more preferably, is formed with a slight curvature (see FIG. 1) to better accommodate the lower extremity. It is also contemplated that the base board 12 has a flat bottom surface to maintain the device stationary and a curved upper surface to better accommodate the lower extremity. The base board 12 may be formed from polyethylene or another conventional material sufficient to allow the base board 12 to function as a rigid supporting base.

A reinforcing plate 14 may be fastened to the bottom portion of the base board 12 by rivets 16. The reinforcing plate 14 provides additional structural support for the base board near the portion where the boot 30 is to be attached. The reinforcing plate 14 may be, for example, aluminum and positioned in the bottom third of the base board 12 and attached by copper rivets 16.

An upright plate 18 is positioned at a right angle to the base board 12 and the reinforcing plate 14, if present, and is attached thereto by fastening angles 20 provided with angle screws 22. The upright plate 18 may be constructed from the same material as the reinforcing plate 14 such as, for example, aluminum. The upright plate 18 has a track 24 formed therein. The track 24 is formed as a slot or groove which extends through the upright plate 18 and is in the form of substantially at least a 180° semicircle (see FIG. 2).

Figure 3:
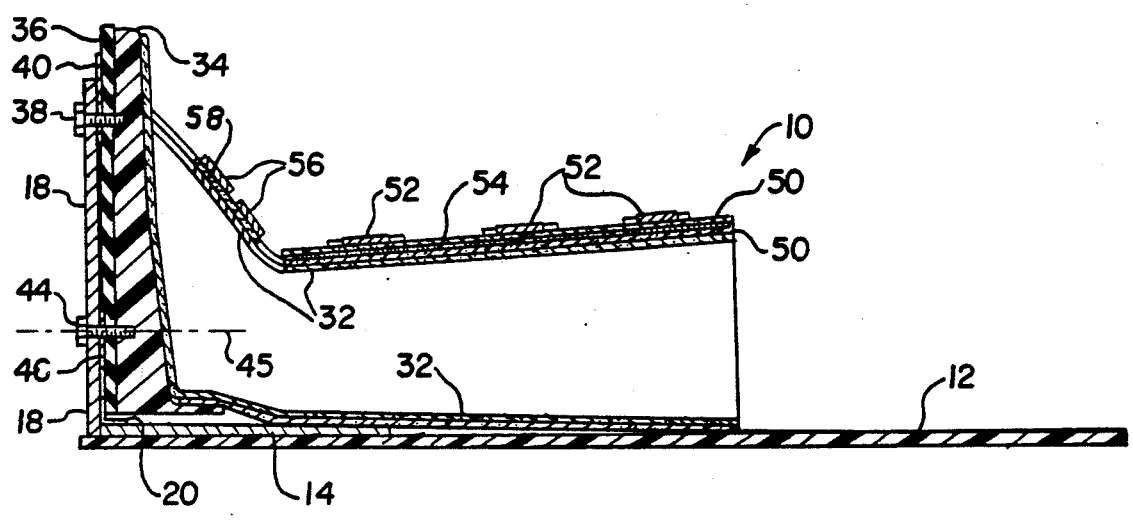
FIG. 3 is a sectional, side view of the positioning device taken along sectional line AA of FIG. 2.

As shown in FIG. 3, the boot 30 includes a removable, soft internal wrap 32 that extends the entire length of the tibia and includes the ankle, instep and plantar surface up to the metatarsals. The internal wrap 32 provides for cushioning of the lower extremity within the boot 30. The boot 30 is provided with a shaped subsole 34 preferably made of polyethylene. The forefoot plantar surface is additionally padded with extremely soft rubber padding 36 which is glued to the shaped subsole 34.

A positioning screw 38 is attached to boot 30 by threadingly engaging the rubber padding 36 and subsole 34. A positioning screw plate 40 is attached to the rubber padding 36 and subsole 34 by rivets 42. The positioning screw 38 extends through track 24 with the head of the screw 38 being larger than the track 24 (see FIG. 3) such that the boot may be attached to the plate 18 by tightening the positioning screw 38, thereby clamping the plate 18 between the positioning screw head and the screw plate 40. A fastening screw 44 is attached to the boot 30 by threadingly engaging the rubber padding 36 and subsole 34 and includes a longitudinal screw axis 45. A fastening screw plate 46 is attached to the sole 36 and subsole 34 by rivets 48. The fastening screw 44 serves to attach the boot 30 to the plate 18 by clamping the plate 18 between the fastening screw 44 and fastening screw plate 46. The fastening screw 44 is positioned at the center of curvature of the track 24 such that the positioning screw 38 moving within track 24 will pivot the boot assembly about the longitudinal axis 45 of the screw as shown by arrow 70 (see FIG. 2).

Marking indicia 64 may be provided adjacent the track 24 to allow for precise positioning of the boot in specific orientations. This indicia would be particularly useful where the diagnostic procedure involves a series of orientations of the boot and lower extremity which involve incremental changes of the rotational orientation of the boot and lower extremity. Furthermore, the indicia allow for exact duplication of a specific orientation of the boot and lower extremity in successive procedures.

The boot 30 also includes a rigid outer boot 50 upon which a plurality of positioning straps 52 and 56 may be attached. A plurality of positioning straps 52 located along the tibia section of the boot are provided with strap loops 53 and Velcro ® 54 (see FIG. 3) for securing the straps in a conventional fashion. A plurality of positioning straps 56 located on the foot portion of the boot 30 are also provided with Velcro ®58 for conventional fastening. The plurality of positioning straps 52 and 56, combined with the soft internal wrap 32, securely locate the lower extremity within the boot and limit movement thereof within the boot 30. Locking straps 66 are attached to the boot through attaching means 68 and are provided to maintain the straps 52 in a closed position.

Figure 4:
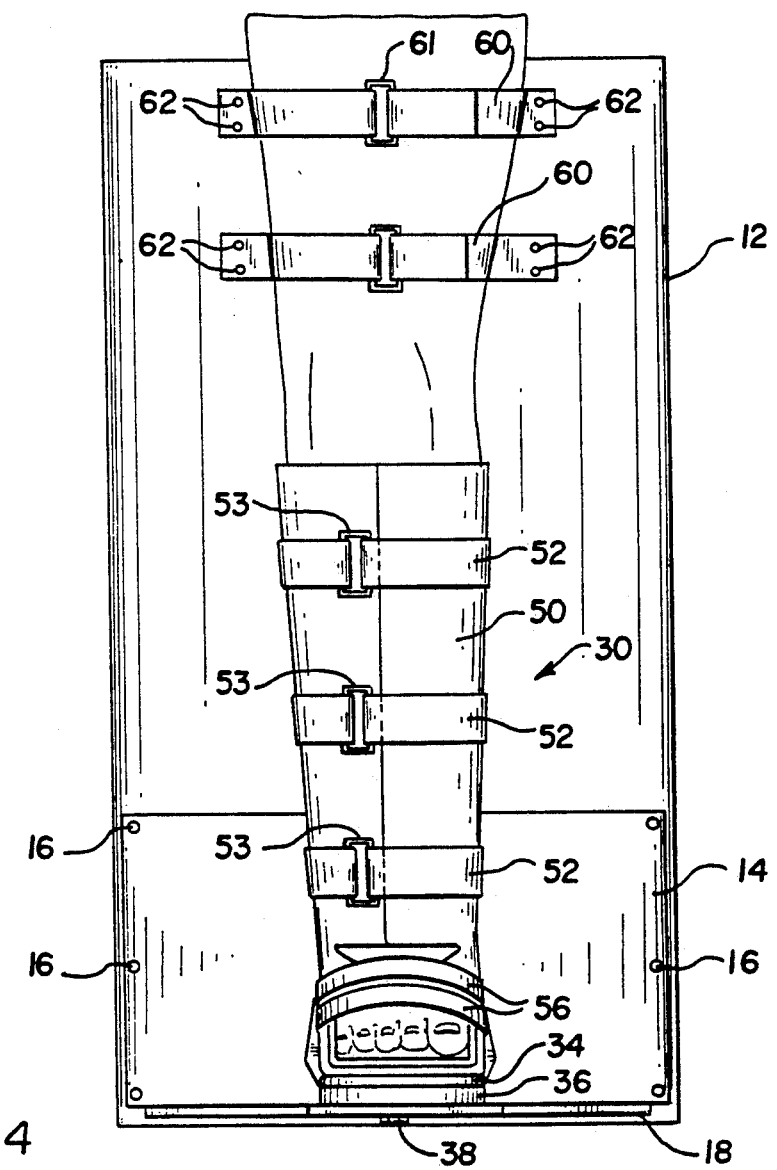
FIG. 4 is a top view of a modified positioning device of the present invention.

As shown in FIG. 4, the positioning device 10 may optionally be provided with a plurality of additional positioning straps 60 which are attached to the base board 12 by rivets 62. These additional positioning straps are located about the thigh portion and are provided with strap loops 61 and conventional fastening means such as Velcro ® (not shown). These additional positioning straps 60 further serve to locate the lower extremity in the desired orientation.

The positioning straps 52, 56 and 60 may be formed from nylon webbing. Padding may be provided on the straps at the contact point with the patient's leg for additional comfort. Natural lamb's wool may be used for such strap padding.

In operation, the lower extremity is positioned within the boot 30 and is firmly located therein by tightening positioning straps 52 and 56. Positioning straps 52 are held in position by locking strap 66. Positioning screw 38 is loosened, if needed, to allow for movement of the boot 30 within the track 24 and fastening screw 44 is rotated to a point which will allow for pivoting of the boot 30. The boot and lower extremity are moved into the desired orientation by pivoting the boot 30 about axis 45 as demonstrated by arrow 70. When the boot 30 and lower extremity are positioned in the desired rotational orientation, the positioning screw 38 is tightened to securely lock the boot 30 and lower extremity onto the plate 18 at that desired orientation. At this point, fastening screw 44 may be further tightened; however, this may not be needed since positioning screw 38 should be sufficient to maintain the boot 30 and lower extremity in the proper orientation. After the boot 30 and lower extremity are in the desired position, the thigh positioning straps 60, if utilized, are tightened and fastened.

While the foregoing describes the present invention with particularity, it will be readily apparent to those of ordinary skill in the art that modifications are possible. Accordingly, and in accordance with the Patent Laws, the scope of the present invention is intended as described in the following claims.

We claim:

1. A positioning device for holding a lower extremity in a specific hip orientation, said positioning device comprising:
    a rigid base board adapted to support said positioning device,
    a plate rigidly attached to a first end of said base board forming an angle of about 90° with respect to said base board,
    a boot for receiving the lower extremity, said boot including a plurality of positioning straps to hold the lower extremity stationary within said boot,
    at least one thigh strap attached to a second end of said base board to secure the thigh of the extremity to said base board, and
    locking means attached to said boot for positioning and locking said boot onto said plate at various orientations relative to said plate.

2. A positioning device of claim 1 wherein said locking means includes a track formed in said plate and a positioning screw, which is threadingly engaging said boot, which is adapted to ride in said track, wherein said positioning screw may be loosened to allow for positioning of said boot by moving said positioning screw along said track and may be tightened to lock said boot relative to said plate at a desired orientation.

3. The positioning device of claim 2 wherein a fastening screw is provided to pivotably attach said boot to said plate, wherein said track is formed as a an arc with a center of curvature at the longitudinal axis of said fastening screw.

4. The positioning device of claim 3 wherein said arcuate track is substantially at least 180°.

5. The positioning device of claim 3 wherein marking indicia are provided on said plate adjacent said track.

6. The positioning device of claim 1 wherein said boot includes a locking strap adapted to lock a plurality of said positioning straps in position.

7. The positioning device of claim 1 wherein at least one of said plurality of positioning straps is positioned on a foot portion of said boot, wherein at least one of said plurality of positioning straps is positioned on a tibial section of said boot.

8. The positioning device of claim 2 wherein said boot comprises a shaped subsole with a soft rubber padding attached thereto.

9. The positioning device of claim 8 wherein said boot comprises a removable internal wrap and a stiff outer boot.

10. The positioning device of claim 9 wherein a fastening screw is provided to pivotably attach said boot to said plate, wherein said track is formed as a an arc with a center of curvature at the longitudinal axis of said fastening screw.

11. The positioning device of claim 10 wherein marking indicia are provided on said plate adjacent said track.

12. The positioning device of claim 11 wherein a reinforcing plate is attached to a bottom portion of said base board.

* * * * *

UNITED STATES PATENT AND TRADEMARK OFFICE
CERTIFICATE OF CORRECTION

PATENT NO. : 5,267,949

DATED : December 7, 1993

INVENTOR(S) : Manuel De La Torre and Thomas K. Donaldson

It is certified that error appears in the above-indentified patent and that said Letters Patent is hereby corrected as shown below:

Claim 3 Line 37 Column 4 "a an arc" should read --an arc--.

Claim 10 Line 59 Column 4 "a an arc" should read --an arc--.

Signed and Sealed this

Third Day of May, 1994

*Attest:*

BRUCE LEHMAN

*Attesting Officer*     *Commissioner of Patents and Trademarks*